United States Patent
Meyer-Boehm et al.

(10) Patent No.: US 11,980,218 B2
(45) Date of Patent: May 14, 2024

(54) DUST-FREE COLD-WATER-DISPERSIBLE PREPARATIONS

(71) Applicant: BASF SE, Ludwigshafen am Rhein (DE)

(72) Inventors: Kathrin Meyer-Boehm, Ludwigshafen am Rhein (DE); Andreas Habich, Ludwigshafen am Rhein (DE); Daniel Wagner, Lampertheim (DE); Wolf Pelletier, Lampertheim (DE); Walter Dobler, Ludwigshafen am Rhein (DE); Peter Schording, Bubenheim (DE); Karl Kolter, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 335 days.

(21) Appl. No.: 17/256,385

(22) PCT Filed: May 29, 2019

(86) PCT No.: PCT/EP2019/063894
§ 371 (c)(1),
(2) Date: Dec. 28, 2020

(87) PCT Pub. No.: WO2020/001906
PCT Pub. Date: Jan. 2, 2020

(65) Prior Publication Data
US 2021/0153540 A1 May 27, 2021

(30) Foreign Application Priority Data

Jun. 27, 2018 (EP) .................................... 18180115

(51) Int. Cl.
| | | |
|---|---|---|
| *A23P 10/47* | (2016.01) | |
| *A23L 33/10* | (2016.01) | |
| *A61K 8/02* | (2006.01) | |
| *A61K 8/25* | (2006.01) | |
| *A61K 9/16* | (2006.01) | |

(52) U.S. Cl.
CPC .............. *A23P 10/47* (2016.08); *A23L 33/10* (2016.08); *A61K 8/022* (2013.01); *A61K 8/25* (2013.01); *A61K 9/1611* (2013.01); *A61K 9/1682* (2013.01); *A61K 2800/10* (2013.01); *A61K 2800/412* (2013.01); *A61K 2800/612* (2013.01); *A61K 2800/621* (2013.01); *A61K 2800/63* (2013.01)

(58) Field of Classification Search
None
See application file for complete search history.

(56) References Cited

U.S. PATENT DOCUMENTS

| | | | |
|---|---|---|---|
| 4,242,219 A | 12/1980 | Bogerman | |
| 4,486,435 A | 12/1984 | Schmidt et al. | |
| 5,290,567 A | 3/1994 | Schneider et al. | |
| 6,221,921 B1* | 4/2001 | Lombardi | C09K 23/017 106/287.11 |
| 2002/0110599 A1 | 8/2002 | Auweter et al. | |
| 2005/0118208 A1 | 6/2005 | Bewert et al. | |
| 2006/0008533 A1* | 1/2006 | Habich | A23L 27/77 424/489 |
| 2009/0312439 A1 | 12/2009 | Hofmann et al. | |
| 2010/0016443 A1 | 1/2010 | Toledano et al. | |
| 2012/0093904 A1 | 4/2012 | Roth et al. | |
| 2015/0283059 A1 | 10/2015 | Nagare et al. | |
| 2019/0090529 A1 | 3/2019 | Meyer-Boehm et al. | |
| 2022/0080026 A1 | 3/2022 | Coulter et al. | |

FOREIGN PATENT DOCUMENTS

| | | |
|---|---|---|
| CN | 101484140 A | 7/2009 |
| CN | 105828806 A | 8/2016 |
| CN | 108697149 A | 10/2018 |
| DE | 10311585 A1 | 9/2004 |
| EP | 1574534 A1 | 9/2005 |
| EP | 2910237 A1 | 8/2015 |
| JP | 05-200273 A | 8/1993 |
| JP | 2002-255931 A | 9/2002 |
| JP | 2013-500280 A | 1/2013 |
| JP | 2014-097935 A | 5/2014 |
| WO | 2018/069204 A1 | 4/2018 |

OTHER PUBLICATIONS

International Preliminary Report on Patentability received for PCT Patent Application No. PCT/EP2019/063894, dated Jan. 7, 2021, 15 pages (9 pages of English Translation and 6 pages of Original Document).
International Search Report and Written Opinion received for PCT Patent Application No. PCT/EP2019/063894, dated Sep. 11, 2019, 20 pages (9 pages of English Translation and 11 pages of Original Document).

* cited by examiner

*Primary Examiner* — Dominic Lazaro
(74) *Attorney, Agent, or Firm* — Faegre Drinker Biddle & Reath LLP

(57) ABSTRACT

The present invention relates to dust-free preparations dispersible in cold water. These preparations consist of particles comprising water-insoluble or only sparingly water-soluble active substance(s), said particles being coated with one or more layers, the outermost layer comprising as principal component one or more hydrophobic powdering agents on which at least one dispersant is absorbed. The invention also relates to a process for producing these particles and to the use thereof in food supplements, foodstuffs, animal feeds, personal-care products, and medicaments.

13 Claims, No Drawings

DUST-FREE COLD-WATER-DISPERSIBLE PREPARATIONS

CROSS-REFERENCE TO RELATED APPLICATIONS

This application is a national stage application (under 35 U.S.C. § 371) of PCT/EP2019/063894, filed May 29, 2019, which claims benefit of European Application No. 18180115.0, filed Jun. 27, 2018, both of which are incorporated herein by reference in their entirety.

The present invention relates to a dust-free preparation that is dispersible in cold water, and to the production and use thereof.

A difficulty in the production of preparations comprising water-insoluble or only sparingly water-soluble active substances, which according to the invention also include preparations comprising vitamin A, vitamin D, vitamin E, and vitamin K and derivatives thereof and preparations comprising carotenoids and mixtures of such preparations, is that, during the final drying process, which is carried out by spray agglomeration, they form blackberry-like, fragile, highly branched structures with an average particle size of approx. 150 µm that generate large amounts of dust, with mechanical stress increasing their high fines fraction (particles <100 µm) still further through breakage of the highly fragile structures.

Against this background, the object of the present invention was to provide preparations consisting of largely dust-free particles that are dispersible in cold water.

This object is achieved by a preparation consisting of particles, the particles having at least one shell layer that comprises as the principal constituent one or more hydrophobic powdering agents and which envelops the active substance-containing particle core. The proportion of this shell layer in the particle is preferably within a range from 0.5% to 8% by weight, more preferably within a range from 0.8% to 6% by weight, and particularly preferably within a range from 1% to 5% by weight.

Suitable hydrophobic powdering agents are finely divided oxides that have been hydrophobized according to the invention and in particular here the hydrophobized oxides of the elements silicon, aluminum or titanium, or mixed oxides of said elements or mixtures of said oxides. Preference is given here to hydrophobized fumed or precipitated silica and in particular here to hydrophobized precipitated silica.

The hydrophobized oxides according to the invention, and in particular here the hydrophobized oxides of the elements silicon, aluminum or titanium, mixed oxides thereof, and mixtures of said oxides, have a BET value of at least 80 $m^2/g$ and/or an average particle diameter d50 of not more than 20 µm. The average particle diameter is generally between 10 nm and 20 µm.

Preference in accordance with the invention is given to hydrophobized fumed or precipitated silicas having a BET value of at least 80 $m^2/g$ and/or an average particle diameter d50 of not more than 20 µm and in particular here the hydrophobized precipitated silica, for example Sipernat D-17, having a BET value of 100 $m^2/g$ and an average particle diameter d50 of 10 µm, determined by laser diffraction in accordance with ISO 13320-1.

The shell layer of hydrophobic powdering agent is preferably applied such that it completely envelops the particle core. The degree of coverage of the particles is, according to SEM image analysis, at least 70%, preferably at least 75%, and more preferably at least 80%, the particle core having an average particle diameter of 140-400 µm.

SEM images were produced using a Zeiss Ultra 55 instrument. Detector: Topographic images with secondary electrons (at 8 kV).

Sample Preparation:
a) Preparation of surfaces: Fixing: Leit C-Tab, coating: approx. 12 nm Pt
b) Preparation of sections: Fixing: Embedding in epoxy resin (EpoFix from Struers, No. 40200029), section with ultramicrotome at RT, coating: approx. 1 carbon filament The shell layer comprising the hydrophobic powdering agent may be applied directly onto the particle core or atop one or more underlying further shell layers.

Production affords largely dust-free particles characterized by a low dust number of less than 15, but preferably a dust number of less than 10, and more preferably of less than 8. The dust number of the coated particles is determined using a DustView II dust measuring device from Palas GmbH, Karlsruhe, Germany.

The device used for the measurement consists of a sample funnel with hatch, a downpipe and a dust chamber with removable dust box.

In the determination of the dust number, the dust-generating solids fractions formed after defined stressing of the material (free fall and impact) are recorded quantitatively.

The evaluation is performed optoelectronically, since the dust-generating solids fraction results in attenuation of a light beam, this attenuation being detected photometrically. The measured value is recorded and evaluated in the control unit. The following measured values are displayed on the control unit as numerical values:

1. Measured value after 0.5 seconds (maximum value)
2. Measured value after 30 seconds (dust value)
3. Dust number (sum of maximum value and dust value)

The dust numbers are assessed as follows:
Dust number 25-100 dust-generating to strongly dust-generating
Dust number 12-25 weakly dust-generating to dust-generating
Dust number 8-12 weakly dust-generating
Dust number <8 virtually dust-free to dust-free.

The particles obtained after coating with hydrophobic powdering agent meet the criterion of freedom from dust but, because of the hydrophobic coating, are not water-dispersible.

In order to make the particles dispersible in cold water, it is necessary according to the invention to apply onto the hydrophobic shell layer of powdering agent a further substance, hereinafter referred to as dispersant, and to apply this uniformly onto the hydrophobic shell layer. The dispersant is absorbed by the hydrophobic shell layer, but may also form a further shell layer, depending on the amount applied.

The dispersant—mixtures of such dispersants can of course also be used—affords particles exhibiting spreading in °, determined by contact-angle measurement after 0.1 seconds at 25° C. on a pellet of pure powdering agent, performed in the present case on pellets of Sipernat D17, of less than or equal to 75°, preferably less than or equal to 70°, and more preferably less than or equal to 60°.

In addition to the dispersant or dispersant mixture as the principal component, further substances may be added to the dispersant. If used, the substances chosen must however not increase the contact angle by more than 15% compared to the pure principal component.

The contact angle of the dispersants is determined on a pellet of Sipernat D17. Substances that are liquid at room temperature are measured at RT (25° C.) and substances that are highly viscous or semi-solid at RT are heated to 60° C. and then measured at RT. For this, a droplet of the sample substance is dropped onto the pellet from a height of 1.5 cm at RT using a disposable syringe (needle diameter 1.65 mm). The contact angle formed between the droplet and the pellet is determined using the OCAH 150 plus from Dataphysics. This is done using the sessile drop method, with the measured data evaluated by ellipse fitting.

Applying the dispersant or dispersant mixture to the hydrophobic shell layer results in a further reduction in the dust number of the particles obtained. Production affords particles characterized by a dust number of less than 10, but preferably by a dust number of less than 8, and more preferably by a dust number of less than 5.

Surprisingly suitable as dispersants in accordance with the invention are in particular those substances that, in addition to the described spreading, have an HLB value of 0.5 to 13, preferably of 1 to 12.5, and more preferably of 1 to 5.5. Particularly preferred dispersants are MCT oil and/or propylene glycol monolaurate (Lauroglycol FCC), i.e. hydrophobic substances that would not be expected to promote dispersibility in cold water, and/or Lutensols, which are amphiphilic in character.

The proportion of dispersant in the overall particle of the preparation is preferably within a range from 0.5% to 6% by weight, more preferably 1% to 4.5% by weight, and particularly preferably from 1.5% to 3% by weight.

The average diameter d50 of the coated particles produced is preferably <400 μm. In a specific embodiment, 140≤d50≤300 μm, more preferably 150≤d50≤275 μm. The d10 value of the cumulative distribution of the size distribution curve of the granulate used is preferably >90 μm. In a specific embodiment, 90≤d10≤125 μm, more preferably 95≤d10≤110 μm. The d90 value of the cumulative distribution of the size distribution curve of the granulate used is preferably <550 μm. In a specific embodiment, 275≤d90≤540 μm, more preferably 285≤d90≤500 μm.

By way of comparison, the particle sizes of the dust-generating preparations in which the final drying process is carried out by spray agglomeration and results in the formation of blackberry-like, fragile, highly branched structures are d10=84 μm, d50=137 μm, and d90=217 μm In the context of the invention, the particle sizes of the particles were determined by laser diffraction using the Mastersizer 2000 instrument from Malvern.

When a silicon-containing, hydrophobic powdering agent such as Sipernat D-17 is employed, with application using MCT oil as dispersant, the Si/MCT ratio, calculated from the quotient of g/100 g Si and % MCT, is within a range from 0.2 to 1.2, preferably 0.25 to 1.0, and more preferably has values from 0.35 to 0.9. The Si content is determined by ICP-OES (inductively-coupled plasma optical-emission spectroscopy) at Si wavelengths of 251 and 611 nm (instrument: Varian Vista 725-ES IP-OES (radial)).

A further advantage of the particles according to the invention is not foaming, or not foaming to an appreciable degree; this is established by determining how rapidly the foam formed during dispersion of the particles breaks down. For the measurement, a 250 ml beaker is charged with 90 g of demineralized water and this is thermally equilibrated in a water bath at a nominal temperature of 25° C. 10 g of the appropriate particles is then added, with magnetic stirring, and stirring is continued until there is no longer any solid visible on the surface of the liquid. The magnetic stirrer is then removed and the mixture is thoroughly mixed with the Ultra-Turrax for 2 minutes on setting 1 (4000 rpm). Care is taken to ensure here that both liquid and air pass into the dispersing tool through the slot in the shaft. Immediately after mixing with the Ultra-Turrax, the foamy solution is transferred to a 250 ml measuring cylinder and the initial volume is determined. Further readings are taken 10 minutes and 1, 2, 3, and 4 hours after the time of transfer. The foam factor is calculated from the ratio of the total filling height, i.e. the total volume of foam and liquid, divided by the volume of the liquid. It is a feature of the particles according to the invention that they form a poorly stable foam during dispersion. After standing for just 1 hour, the foam has almost completely broken down, with the result that the foam factor determined after 1 hour is less than or equal to 1.2.

For the purposes of the invention, water-insoluble or only sparingly water-soluble active substances are to be understood as meaning substances for which the saturation solubility at RT (25° C.) in at least one of the following media is less than 1% by weight: water, 0.1 M aqueous hydrochloric acid, aqueous phosphate buffer pH 7.2, 0.9% by weight aqueous sodium chloride solution.

Water-insoluble or only sparingly water-soluble active substances that are suitable for use in accordance with the invention accordingly include a large number of active substances and effect substances, in particular pharmaceutical or cosmetic active substances, active substances for food supplements or dietary agents or food additives.

Examples of sparingly soluble substances for the purposes of the invention are:

piroxicam, clotrimazole, carbamazepine, 17-beta-estradiol, sulfathiazole, fenofibrate, benzocaine, lidocaine, dimetindene, biperiden, bisacodyl, clioquinol, droperidol, haloperidol, nifedipine, nitrendipine, tetracycline, phenytoin, glafenine, floctafenine, indometacin, ketoprofen, ibuprofen, dipyridamole, mefenarnic add, amiodarone, felodipine, itraconazole, ketoconazole, danazol, furosemide, tolbutamide, ritonavir, lopinavir, naproxen, spironolactone, propafenone, progesterone, paclitaxel, docetaxel, theophylline, hydrocortisone, β-carotene, canthaxanthin, astaxanthin, zeaxanthin, lutein, lycopene, capsanthin, capsorubin, α- and β-cryptoxanthin, citranaxanthin, bixin, echinenone, β-apo-4-carotenal, β-apo-8-carotenal, β-apo-8-carotene esters, vitamin A, tocopherol acetate, riboflavin, vitamin Q10, vitamin D, vitamin K, disulfiram, nimodipine, chlorothiazide, chlorpropamide, dicoumarol, chloramphenicol, digoxin, lonidamine, pizotifen, atovaquone, amprenavir, bexarotene, calcitriol, clofazimine, doxercalciferol, dronabinol, dutasteride, etoposide, loratadine, risperidone, saquinavir, sirolimus, valproic acid, amphotericin, alprostadil, carmustine, chlordiazepoxide, fenoldopam, melphalan, methocarbamol, oxytetracycline, docetaxel, fulvestrant, propofol, voriconazole, ziprasidone, leuprorelin acetate, Viadur, valrubicin, tramadol, celecoxib, etodolac, rofecoxib, oxaprozin, leflunomide, diclofenac, nabumetone, ibuprofen, flurbiprofen, tetrahydrocannabinol, capsaicin, ketorolac, albendazole, ivermectin, amiodarone, zileuton, zafirlukast, salbutamol, montelukast, azithromycin, ciprofloxacin, clarithromycin, dirithromycin, rifabutin, rifapentine, trovafloxacin, baclofen, ritonavir, saquinavir, nelfinavir, efavirenz, dicoumarol, tirofiban, cilostazol, ticlopidine, clopidogrel, oprelvekin, paroxetine, sertraline, venlafaxine, bupropion, clomipramine, miglitol, repaglinide, glimepiride, pioglitazone, rosiglitazone, troglitazone, glyburide, glipizide, glibenclamide, fosphenytoin, tiagabine, topirarnate, larnotrigine, vigabatrin, amphotericin B, butenafine, terbinafine, itraconazole, fluconazole, miconazole, ketoconazole, metronidazole, griseofulvin, nitrofurantoin, lisinopril, benazepril, nifedipine, nisoldipine, telmisartan, irbesartan, eprosartan, valsartan, candesartan, minoxidil, terazosin, halofantrine, mefloquine, dihydroergotamine, ergotamine, frovatriptan, pizotifen, sumatriptan, zolmitriptan, naratriptan, rizatriptan, aminoglutethimide, busulfan, cyclosporine, mitoxantrone, irinotecan, etoposide, teniposide, paclitaxel, tacrolimus, siroiimus, tamoxifen, camptothecin, topotecan, nilutamide, bicalutamide, toremifene, atovaquone, metronidazole, furazolidone, paricalcitol, benzonatate, midazolam, zolpidem, gabapentin, zopiclone, digoxin, beclometasone, budesonide, betamethasone, prednisolone, cisapride, cimetidine, loperamide, famotidine, lansoprazole, rabeprazole, nizatidine, orneprazole, cetirizine, cinnarizine, dexchlorpheniramine, loratadine, clemastine, fexofenadine, chlorphenamine, acitretin, tazarotene, calcipotriol, calcitriol, Targretin, ergocalciferol, cholecalciferol, isotretinoin, tretinoin, calcifediol, fenofibrate, probucol, gemfibrozil, cerivastatin, pravastatin, simvastatin, fluvastatin, atorvastatin, tizanidine, dantrolene, isosorbide dinitrate, dihydrotachysterol, essential fatty acids, codeine, fentanyl, methadone, nalbuphine, pentazocine, clomifene, danazol, dihydroepiandrosterone, medroxyprogesterone, progesterone, rimexolone, megestrol acetate, estradiol, finasteride, mifepristone, l-thyroxine, tamsuiosin, methoxsalen, tacrine, donepezil, raloxifene, vertepofin, sibutramine, pyridostigmine, and isomers, derivatives, salts, or mixtures thereof.

Particular preference is given to the carotenoids β-carotene, canthaxanthin, astaxanthin, zeaxanthin, lutein, lycopene, capsanthin, capsorubin, α- and β-cryptoxanthin, citranaxanthin, bixin, echinenone, β-apo-4-carotenal, β-apo-8-carotenal, β-apo-8-carotene esters, vitamins A, D, K and tocopherol acetate, and isomers, derivatives, salts, or mixtures thereof.

The content of the water-insoluble or only sparingly water-soluble active substances in the preparations of the invention is within a range from 0.1% to 60% by weight, preferably within a range from 0.2% to 50% by weight, particularly preferably within a range from 0.5% to 25% by weight, very particularly preferably within a range from 1% to 20% by weight, based on the dry mass of the preparation.

In the case of the carotenoids β-carotene, canthaxanthin, astaxanthin, zeaxanthin, lutein, lycopene, capsanthin, capsorubin, α- and β-cryptoxanthin, citranaxanthin, bixin, echinenone, β-apo-4-carotenal, β-apo-8-carotenal, β-apo-8-carotene esters, vitamins A, D, K and tocopherol acetate, and isomers, derivatives, salts, or mixtures thereof, the content in the preparations of the invention is particularly preferably from 0.5% to 25% by weight and very particularly preferably from 1% to 20% by weight.

To increase the stability of the preparations comprising water-insoluble or only sparingly water-soluble active substances, it is advantageous to incorporate protective colloids, softeners, and/or stabilizers into the active-substance formulation.

Protective colloids used are plant gums, modified plant gums, gelatin, modified gelatin, starch, modified starch, lignosulfonate, chitosan, carrageenan, casein, caseinate, whey protein, zein, modified cellulose, pectin, modified pectin, plant proteins and modified plant proteins or mixtures thereof. Polyvinyl alcohol, polyvinylpyrrolidone, methylcellulose, carboxymethyl cellulose, hydroxypropyl cellulose, and alginate may however also be used.

To increase the mechanical stability of the preparation, it is expedient to add a softener to the colloid, such as sugars or sugar alcohols, for example sucrose, glucose, lactose, invert sugar, sorbitol, mannitol, glycerol, Palatinose or mixtures thereof.

The ratio of colloid and softener to carotenoid solution is generally chosen so as to obtain a dry product that contains between 3% and 20% by weight of an active substance, 10% to 50% by weight of a colloid, 20% to 70% by weight of a softener.

To increase the stability of the active substance toward oxidative degradation, it can be advantageous to add 0% to 10% by weight, preferably 0.5% to 8% by weight, based on the dry mass of the formulation, of one or more stabilizers such as α-tocopherol, t-butyl-hydroxytoluene, t-butyl-hydroxyanisole, ascorbic acid, propyl gallate or ethoxyquin.

Emulsifiers may additionally be used, for example ascorbyl palmitate, polyglycerol esters of fatty acids, sorbitan esters of fatty acids, propylene glycol esters of fatty acids or lecithin, at a concentration of 0% to 200% by weight, preferably 5% to 150% by weight, more preferably 10% to 80% by weight, based on the active substance used.

It can sometimes also be advantageous to additionally use a physiologically permissible oil such as sesame oil, maize kernel oil, cottonseed oil, soybean oil or peanut oil or esters of medium-chain vegetable fatty acids in a concentration of 0% to 500% by weight, preferably 10% to 300% by weight, more preferably 20% to 100% by weight, based on the active substance.

The present invention also provides a process for producing the preparations of the invention.

The process comprises the following steps:
a) dissolving the water-insoluble or only sparingly water-soluble active substance(s) in a volatile, water-miscible organic solvent or in a mixture of water and a water-miscible organic solvent at temperatures between 50° C. and 200° C., optionally under elevated pressure, within a period of less than 10 seconds,
b) rapidly mixing the solution obtained after a) with an aqueous or colloidally dispersed solution of a colloid at temperatures between 0° C. and 50° C., wherein the water-insoluble or only sparingly water-soluble active substance(s) is/are precipitated in colloidally dispersed form,
c) spraying the colloidal dispersion with additional use of a hydrophobic powdering agent and converting this into a dry powder by removing the bulk of the solvent and then drying, and
d) applying at least one dispersant to the free-flowing particles or
a2) dissolving the water-insoluble or only sparingly water-soluble active substance(s) in a volatile, water-immiscible organic solvent at temperatures of 30 to 150° C., optionally under elevated pressure,
b2) mixing the solution obtained after a) with an aqueous or colloidally dispersed solution of a colloid, forming an emulsion,
c2) removing the organic solvent from the emulsion, adding hydrophobic powdering agent to the suspension/dispersion formed, and converting this into a dry powder by removing the water and then drying, and
d2) applying at least one dispersant to the free-flowing particles.

The solvents suitable for executing the process of the invention are primarily water-miscible, thermally stable, volatile solvents that contain only carbon, hydrogen, and oxygen, such as alcohols, ethers, esters, ketones, and acetals. Preference is given to using ethanol, n-propanol, isopropanol, butane-1,2-diol 1-methyl ether, propane-1,2-diol 1-n-propyl ether or acetone. It is expedient to generally use solvents that are at least 10% miscible with water, have a boiling point below 200° C., and/or have fewer than 10 carbon atoms.

Depending on the type and amount of the protective colloid used, a deeply colored viscous liquid is obtained after process step b) or b2). The solvent may be removed for example by extraction with a water-immiscible solvent or, depending on the boiling point, in a manner known per se, for example by distillation, optionally under reduced pressure. In this instance it has been found to be expedient and possible to use as solvent directly the azeotrope obtained when using isopropanol, without the removal of water. However, it is preferable to remove the solvent alongside the removal of water, by spray drying or spray granulation.

The pulverulent preparation of the invention is suitable, inter alia, as an additive to food preparations, for example for coloring foodstuffs such as beverages, as a means for producing pharmaceutical and cosmetics preparations, and also for producing food supplement preparations, for example multivitamin preparations in the human and animal sectors.

The present invention further provides for the use of the above-described pulverulent formulation of the invention as an additive to animal feeds, foodstuffs, food supplements, personal-care products or pharmaceutical compositions.

The present invention likewise provides animal feeds, foodstuffs, food supplements, personal-care products or pharmaceutical compositions comprising the pulverulent preparation of the invention.

The invention is elucidated by the example that follows, which does not restrict the invention in any way:

EXAMPLE

1. Astaxanthin, ascorbyl palmitate, and tocopherol are dissolved in an azeotropic mixture of water and isopropanol at a temperature of 100° C. to 200° C. and a pressure between 20 bar and 100 bar within a period of less than 10 seconds.
2. Sodium caseinate, glucose syrup, sodium ascorbate, and preservatives are dissolved in water.
3. The mixture from 2. is treated with approx. 1% NaOH.
4. The preparation from 1. and 2. is mixed at temperatures between 20° C. and 80° C., resulting in the astaxanthin precipitating and becoming encapsulated/enveloped.
5. Isopropanol and some of the water are removed in a multistage evaporation at pressures below atmospheric pressure, resulting in the formation of a 15 to 65 percent by weight (suspension) dispersion.
6. This dispersion is sprayed in together with hydrophobic silica at the head of a spray tower, resulting in the formation of fine droplets that are enveloped by hydrophobic silica.
7. Drying takes place in a downstream fluidized bed.
8. In the following step, MCT oil is sprayed on.

The coated free-flowing particles obtained as the end product in accordance with the invention have a dust value of 2.4 and a D50 of 170 μm. The silicon content is 1.4% and the MCT content is 2.4%, which corresponds to a ratio of Si in % to MCT in % of 0.58. The contact angle of the particles measured after 0.1 seconds and at 25° C. against the surface of a Sipernat D17 pellet is 54°.

The invention claimed is:

1. A particle comprising at least one water-insoluble or only sparingly water-soluble active substance that is coated with one or more layers, wherein the outermost one or more layers comprises one or more hydrophobic powdering agents on which at least one dispersant is absorbed;
   in which the at least one dispersant has an HLB value of 0.5 to 13;
   in which the hydrophobic powdering agent is hydrophobized silica; and
   wherein the at least one dispersant comprises medium chain triglyceride (MCT) oil and in which the ration of hydrophobized silica to MCT oil is 0.2 to 1.2 based on 100 g of particles.
2. The coated particle according to claim 1, in which the at least one dispersant has a contact angle against the surface of a pellet made of pure powdering agent, measured after 0.1 seconds and at 25° C., of 75° or less.
3. The coated particle according to claim 1, in which the at least one dispersant further comprises propylene glycol monolaurates and/or polyalkyleneglycolethers.
4. The coated particle according to claim 1, in which the degree of coverage of the particle surface with hydrophobic powdering agent is at least 70%.
5. The coated particle according to claim 1, in which the degree of coverage of the particle surface with hydrophobic powdering agent is at least 80%.
6. The coated particle according claim 1, in which the hydrophobic powdering agent has a surface area of at least 80 m$^2$/g.
7. The coated particle according to claim 1, in which the hydrophobic powdering agent has an average particle size of not more than 20 μm.
8. The coated particle according to claim 7, in which the hydrophobic powdering agent has an average particle size of 10 nm to 20 μm.
9. A preparation consisting of the coated particles according to claim 1, said preparation having a dust value after 30 seconds of less than 10.
10. A process for producing particles according to claim 1, the process comprising the following steps:
    a) dissolving the water-insoluble or only sparingly water-soluble active substance(s) in a volatile, water-miscible organic solvent or in a mixture of water and a water-miscible organic solvent at temperatures between 50° C. and 200° C., optionally under elevated pressure, within a period of less than 10 seconds,
    b) rapidly mixing the solution obtained after a) with an aqueous or colloidally dispersed solution of a colloid at temperatures between 0° C. and 50° C., wherein the water-insoluble or only sparingly water-soluble active substance(s) is/are precipitated in colloidally dispersed form,
    c) spraying the colloidal dispersion with additional use of a hydrophobic powdering agent and converting this into a dry powder by removing the bulk of the solvent and then drying, and
    d) applying at least one dispersant to the free-flowing particles or
    a2) dissolving the water-insoluble or only sparingly water-soluble active substance(s) in a volatile, water-immiscible organic solvent at temperatures of 30 to 150° C., optionally under elevated pressure,
    b2) mixing the solution obtained after a) with an aqueous or colloidally dispersed solution of a colloid, forming an emulsion,
    c2) removing the organic solvent from the emulsion, adding hydrophobic powdering agent to the suspension/dispersion formed, and converting this into a dry powder by removing the water and then drying, and d2) applying at least one dispersant to the free-flowing particles.

11. A food supplement, foodstuff, animal feed, personal-care product, or medicament comprising the coated particles according to claim 1.

12. The coated particle according to claim 1, in which the at least one dispersant has an HLB value of 1 to 12.5.

13. The coated particle according to claim 1, in which the at least one dispersant has an HLB value of 1 to 5.

* * * * *